US011471396B2

(12) United States Patent
Jones et al.

(10) Patent No.: US 11,471,396 B2
(45) Date of Patent: *Oct. 18, 2022

(54) PERSONAL CARE COMPOSITIONS COMPRISING SURFACE-MODIFIED PARTICLES AND NON-VOLATILE FUNCATIONALISED SILICONE

(71) Applicant: Conopco, Inc., Englewood Cliffs, NJ (US)

(72) Inventors: Christopher Clarkson Jones, Wirral (GB); Xiaoyun Pan, Shanghai (CN); Su Yuan, Shanghai (CN); Qiqing Zhang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/343,011

(22) PCT Filed: Oct. 4, 2017

(86) PCT No.: PCT/EP2017/075125
§ 371 (c)(1),
(2) Date: Apr. 18, 2019

(87) PCT Pub. No.: WO2018/077578
PCT Pub. Date: May 3, 2018

(65) Prior Publication Data
US 2020/0046628 A1 Feb. 13, 2020

(30) Foreign Application Priority Data
Oct. 28, 2016 (WO) ................ PCT/CN2016/103838

(51) Int. Cl.
*A61K 8/73* (2006.01)
*A61K 8/02* (2006.01)
*A61K 8/892* (2006.01)
*A61K 8/898* (2006.01)
*A61Q 5/12* (2006.01)
*A61Q 13/00* (2006.01)

(52) U.S. Cl.
CPC ............ *A61K 8/736* (2013.01); *A61K 8/0241* (2013.01); *A61K 8/892* (2013.01); *A61K 8/898* (2013.01); *A61Q 5/12* (2013.01); *A61Q 13/00* (2013.01); *A61K 2800/412* (2013.01); *A61K 2800/624* (2013.01)

(58) Field of Classification Search
None
See application file for complete search history.

(56) References Cited

U.S. PATENT DOCUMENTS

| 6,534,091 | B1 | 3/2003 | Garces Garces et al. |
| 6,733,790 | B1 | 5/2004 | Garces Garces |
| 6,818,296 | B1 | 11/2004 | Garces Garces et al. |
| 6,979,467 | B1 | 12/2005 | Garces Garces et al. |
| 2001/0053803 | A1 | 12/2001 | Kuwahara et al. |
| 2006/0073209 | A1 | 4/2006 | Sung et al. |
| 2007/0181038 | A1 | 8/2007 | Sabesan et al. |
| 2007/0286837 | A1* | 12/2007 | Torgerson ............ A61K 8/898 424/70.122 |
| 2009/0013481 | A1 | 1/2009 | Colaco et al. |
| 2009/0258042 | A1 | 10/2009 | Anastasiou |
| 2010/0008870 | A1 | 1/2010 | Dihora et al. |
| 2010/0047202 | A1 | 2/2010 | Goddinger et al. |
| 2010/0173003 | A1 | 7/2010 | SenGupta et al. |
| 2010/0261629 | A1 | 10/2010 | Smets et al. |
| 2011/0071064 | A1 | 3/2011 | Lei et al. |
| 2011/0152147 | A1 | 6/2011 | Smets et al. |
| 2012/0237578 | A1 | 9/2012 | Lei et al. |
| 2014/0079686 | A1 | 3/2014 | Barman et al. |
| 2015/0265541 | A1 | 9/2015 | Park |
| 2016/0099680 | A1 | 4/2016 | Li et al. |
| 2016/0106636 | A1 | 4/2016 | Speaker et al. |
| 2016/0028944 | A1 | 5/2016 | Chawrai et al. |

FOREIGN PATENT DOCUMENTS

| CN | 103889392 | 6/2014 |
| CN | 103747772 | 4/2019 |
| DE | 102007031202 | 3/2009 |
| DE | 102007033184 | 7/2009 |
| DE | 102011079664 | 4/2012 |
| EP | 1257353 | 11/2004 |
| EP | 1813257 | 8/2007 |
| EP | 2865423 | 4/2015 |
| KR | 20070079367 | 8/2007 |
| WO | WO09009657 | 8/1990 |
| WO | WO0147625 | 5/2001 |
| WO | WO0162376 | 8/2001 |
| WO | WO2006041613 | 4/2006 |
| WO | WO2007027711 | 3/2007 |

(Continued)

OTHER PUBLICATIONS

Written Opinion 2 in PCTEP2017075125.
Search Report and Written Opinion in EP16205438; dated Jun. 27, 2017.
Search Report and Written Opinion in PCTEP2017075125; dated Dec. 21, 2017.
IPRP2 in PCTEP2017075125; dated Mar. 12, 2019; World Intellectual Property Org. (WIPO).
Search Report and Written Opinion in PCTEP2017074777; dated Jan. 4, 2018.
Search Report & Written Opinion in EP16205435; dated Feb. 14, 2017.

*Primary Examiner* — Melissa L Fisher

(74) *Attorney, Agent, or Firm* — Greenberg Traurig, LLP

(57) ABSTRACT

Disclosed is a personal care composition comprising (a) particle comprising chitosan salt at the outer surface of the particle; and (b) functionalized non-volatile silicone, wherein the amount of the functionalized non-volatile silicone is greater than 20% by weight of the total non-volatile silicone.

11 Claims, No Drawings

(56) References Cited

FOREIGN PATENT DOCUMENTS

| | | |
|---|---|---|
| WO | WO2008148093 | 12/2008 |
| WO | WO2009020314 | 2/2009 |
| WO | WO2011075556 | 6/2011 |
| WO | WO2012065065 | 5/2012 |
| WO | WO2012177986 | 12/2012 |
| WO | WO2014064121 | 5/2014 |
| WO | WO2015023961 | 2/2015 |
| WO | WO2015051054 | 4/2015 |
| WO | WO2016000912 | 1/2016 |
| WO | WO2016049456 | 3/2016 |
| WO | WO2016180769 | 2/2017 |

\* cited by examiner

PERSONAL CARE COMPOSITIONS COMPRISING SURFACE-MODIFIED PARTICLES AND NON-VOLATILE FUNCATIONALISED SILICONE

FIELD OF THE INVENTION

The present invention is related to a person care composition containing particles. In particular, the present invention is related to a person care composition comprising (a) particle comprising chitosan salt at the outer surface of the particle, and (b) functionalized non-volatile silicone.

BACKGROUND OF THE INVENTION

Many personal care products seek to deliver benefit agents to substrates such as hair, and/or skin. To achieve a long-lasting benefit agent release performance, encapsulation of the benefit agent in particles has been proposed as a means, in particular for the perfume. When applied, the microcapsule may be deposited onto the substrates, for example onto hair, and broken by action of pressure and/or rubbing when consumers wash their hair. The perfume is then released and brings superior sensory to the consumers.

The deposition efficiency of the particles is very important for the delivery of the encapsulated benefit agents. Efforts have been made to provide particles with superior deposition efficiency. However, when the particles are incorporated into a personal care composition, the deposition efficiency may be adversely affected by ingredients of the composition.

Thus, we have recognized that there is a need to develop a personal care composition with a high deposition efficiency of particles. We therefore developed a person care composition comprising (a) particle comprising chitosan salt at the outer surface of the particle, and (b) specific non-volatile silicone. It was surprisingly found that when including the particles and specific silicone of the present invention into a personal care composition, the particles have better deposition efficiency onto hair.

SUMMARY OF THE INVENTION

In a first aspect, the present invention is directed to a personal care composition comprising particle comprising chitosan salt at the outer surface of the particle; and functionalized non-volatile silicone, wherein the amount of the functionalized non-volatile silicone is greater than 20% by weight of the total non-volatile silicone.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Water insoluble" as used herein refers to that the solubility in water is less than 1 gram per 100 gram of water, preferably less than 1 gram per 1 kilogram of water, at 25° C. and at atmospheric pressure.

"Non-volatile" as used herein means having vapour pressure from 0 to 0.1 mm Hg (13.3 Pa), preferably from 0 to 0.05 mm Hg, more preferably from 0 to 0.01 mm Hg at 25° C.

Viscosity for the purposes of the present invention means kinematic viscosity at 25° C. and is reported as centiStokes (1 cSt=1 mm$^2 \cdot$s$^{-1}$) unless otherwise explicitly stated. Viscosity of fluids such as silicone is determined by the relevant international standard, ISO 3104.

One benefit of small particles is that they are less visible in clear products. However, if the particles are too small then it can become difficult to break thereby releasing the benefit agent. Therefore, the particle preferably has an average particle diameter of 0.1 to 50 μm, more preferably from 0.3 to 40 μm, even more preferably from 0.5 to 20 μm, still even more preferably from 1 to 10 μm and most preferably from 1.4 to 6 μm. Diameter of particle means the apparent volume median diameter (D50, also known as x50 or sometimes d(0.5)) of the particles unless otherwise stated. The diameter may be measurable for example, by laser diffraction using a system (such as a Mastersizer™ 2000 available from Malvern Instruments Ltd).

To have a better deposition on hair, the zeta potential of the particles as measured using a Malvern Nano ZS90 apparatus, in DI water at a solid content of 50 ppm and pH of 7 at 25° C., is preferably at least 5 mV, more preferably at least 15 mV, even more preferably at least 20 mV.

The chitosan salt suitable for the present invention comprises a chitosan component and an anion. Preferably the anion is an organic anion and more preferably an organic anion having a molecular weight of greater than 60, more preferably from 80 to 2000, even more preferably from 80 to 500. Preferably, the chitosan salt is a chitosan-amino acid salt. Preferably the amino acid comprises glutamine, glutamic acid, histidine, leucine, lysine, serine, threonine, arginine or a mixture thereof, more preferably comprises arginine. Most preferably, the chitosan salt is chitosan-arginine salt.

Preferably the chitosan component of the salt (as a protonated material) has a viscosity average molecular weight of at least 10,000 Daltons, more preferably in the range of from 30,000 to 1,000,000 Daltons, even more preferably from 70,000 to 600,000 Daltons, and still even more preferably from 150,000 to 400,000 Daltons. Preferably, the deacetylation degree of the chitosan component is at least 65%, more preferably from 70 to 95%, even more preferably from 72 to 90% and most preferably from 75 to 85%.

Preferably, the chitosan component comprises at least 5%, more preferably at least 10% of protonated primary amino group, by mole of the total amount of primary amino group and protonated primary amino group.

Preferably, the chitosan salt is bound to the particle by means of a covalent bond, entanglement or strong adsorption, more preferably by a covalent bond or entanglement, and most preferably by means of a covalent bond. It is important that the chitosan salt is not removed by water from the particle as it cannot then function effectively as a delivery aid. Thus, for example spray-drier coating of chitosan onto particles would not result in chitosan being an effective delivery aid as the chitosan would be removed from the particles on exposure to water. "Entanglement" as used herein refers to that the chitosan salt is adsorbed onto the particle as the polymerization proceeds and the particle grows in size. It is believed that under such circumstances part of the adsorbed chitosan salt becomes buried within the interior of the particle. Hence at the end of the polymerization, part of the chitosan salt is entrapped and bound in the polymer matrix of the particle, whilst the remainder is free to extend into the aqueous phase.

Typically, the particles comprise benefit agent inside of an inner shell, and an outer shell comprising the chitosan salt at the outer surface of the particle. For sake of clarity, it should be noted that the outer shell is different from the inner shell. Preferably at least 20% of the outer shell by weight, more preferably at least 50% of the outer shell by weight, even more preferably at least 80% by weight of the outer shell is chitosan salt. Most preferably, the outer shell is the chitosan salt.

Various benefit agents can be incorporated into the particles. The benefit agents may include fragrance, pro-fragrance, hair conditioning agent, anti-dandruff agent, moisturizers, emollients, dyes and/or pigments, colour care additives (including dye fixing agents), or a mixture thereof. Preferably, the benefit agent comprises fragrance, pro-fragrance, hair conditioning agent or a mixture thereof. More preferably, the benefit agent is fragrance and/or pro-fragrance, and most preferably the benefit agent is fragrance.

Useful components of the fragrance include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Fragrance and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally fragranced or flavoured, or of modifying the odour and/or taste of said consumer product.

By fragrance in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well-known top-notes include citrus oils, linalool, linalyl acetate, lavender, dihydromyrcenol, rose oxide and cis-3-hexanol. Top notes typically comprise 15-25% wt of a fragrance composition and in those embodiments of the invention which contain an increased level of top-notes it is envisaged at that least 20% wt would be present within the particle.

Another group of fragrances with which the present invention can be applied are the so-called 'aromatherapy' materials. These include many components also used in fragrancery, including components of essential oils such as Clary Sage, *Eucalyptus*, Geranium, Lavender, Mace Extract, Neroli, Nutmeg, Spearmint, Sweet Violet Leaf and Valerian.

Typical fragrance components which it is advantageous to employ in the embodiments of the present invention include those with a relatively low boiling point, preferably those with a boiling point of less than 300, preferably 100-250 Celsius, measured at one atmosphere.

It is also advantageous to encapsulate fragrance components which have a low Log P (i.e. those which will be partitioned into water), preferably with a Log P of less than 3.0.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols.

The fragrance is typically present in an amount of from 10-85% by total weight of the particle, preferably from 15 to 75% by total weight of the particle. The fragrance suitably has a molecular weight of from 50 to 500 Dalton. Pro-fragrances can be of higher molecular weight, being typically 1-10 k Dalton.

Typically the inner shell comprises water insoluble non-polysaccharide polymer, water insoluble inorganic salt or a mixture thereof, more preferably the inner shell comprises water insoluble non-polysaccharide polymer. Inorganic salt may be selected from clay, zeolite, silica, amorphous silicate, crystalline nonlayer silicate, layer silicate, calcium carbonate, sodium carbonate, sodalite, and alkali metal phosphates.

Preferably, the water insoluble non-polysaccharide polymer comprises polyvinyl pyrrolidone, polyvinyl alcohol, cellulose ether, polystyrene, polyacrylate, polymethacrylate, polyolefin, aminoplast polymer, polyacrylamide, acrylate-acrylamide copolymer, melamine-formaldehyde condensate, urea-formaldehyde condensate, polyurethane, polysiloxane, polyurea, polyamide, polyimide, polyanhydride, polyolefin, polysulfone, polysaccaharide, polylactide, polyglycolide, polyorthoester, polyphosphazene, silicone, lipid, polyester, ethylene maleic anyhydride copolymer, styrene maleic anyhydride copolymer, ethylene vinyl acetate copolymer, lactide glycolide copolymer, or combinations of these materials. More preferably, the inner shell comprises polystyrene, polyvinyl alcohol, polyacrylate, polymethacrylates, polyolefins, aminoplast polymer, polyacrylamide, acrylate-acrylamide copolymer, melamine-formaldehyde condensate, urea-formaldehyde condensate, polyurethane, polysaccaharide or a mixture thereof. More preferably, the water insoluble non-polysaccharide polymer comprises polystyrene, modified polyvinyl alcohol, polyacrylate, polymethacrylate, polyolefin, aminoplast polymers, melamine-formaldehyde condensate, urea-formaldehyde condensate, polyurethane or a mixture thereof. Even more preferably the water insoluble non-polysaccharide polymer comprises polystyrene, modified polyvinyl alcohol, polyolefin, polyurethane or a mixture thereof. Still even more preferably, the water insoluble non-polysaccharide polymer comprises polystyrene, modified polyvinyl alcohol or a combination thereof and most preferably, the water insoluble non-polysaccharide polymer is polystyrene, modified polyvinyl alcohol, or a combination thereof.

The particle is typically present in the composition at levels of from 0.001% to 10%, preferably from 0.005% to 7.55%, most preferably from 0.01% to 5% by weight of the total composition.

The viscosity of the functionalized non-volatile silicone refers to the viscosity of the functionalized non-volatile silicone itself (not the emulsion, or the final composition or mixture of two silicones). Preferably, the functionalized non-volatile silicone has a kinematic viscosity of from 50 to 20,000,000 cSt, more preferably from 50 to 1,000,000 cSt, even more preferably from 50 to 300,000 cSt, still even more preferably from 100 to 50,000 cSt, and most preferably from 150 to 20,000 cSt at 25° C.

Preferably the functionalized non-ionic silicone is emulsified with emulsifier. Suitable emulsifiers for use in the preparation of the aqueous emulsion are well known in the art and includes anionic emulsifier, cationic emulsifier, nonionic emulsifier or mixtures thereof. More preferably, the emulsifiers are anionic emulsifier, nonionic emulsifier or a mixture thereof.

Examples of anionic surfactants used as emulsifiers for the silicone particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20, alkylphenol ether sulphates, e.g., octylphenol ether sulphate nEO where n is from 1 to 20, and sulphosuccinates, e.g., sodium dioctylsulphosuccinate.

Examples of nonionic surfactants suitable for use as emulsifiers for the silicone droplets are alkylphenol ethoxylates, e.g., nonylphenol ethoxylate nEO, where n is from 1 to 50 and alcohol ethoxylates, e.g., lauryl alcohol nEO, where n is from 1 to 50, ester ethoxylates, e.g., polyoxyethylene monostearate where the number of oxyethylene units is from 1 to 30.

Preferably the functionalized non-volatile silicone suitable for use in the compositions of the invention has a Sauter mean droplet diameter ($D_{3,2}$) of no greater than 1 micron, more preferably no greater than 500 nm, even more preferably no greater than 300 nm, still even more preferably from 10 to 150 nm and most preferably 20 to 100 nm. Silicone Sauter mean droplet diameter ($D_{3,2}$) may be measured by laser light scattering using an instrument such as a Malvern Mastersizer.

Typically, the functionalized non-volatile silicone is present in the composition in amount from 0.01 to 10% by weight of the composition, more preferably from 0.1 to 5% by weight of the composition, even more preferably from 0.3 to 4%, still even more preferably from 0.5 to 3% and most preferably from 0.7 to 2.5% by weight of the composition.

The weight ratio of the particle to functionalized non-volatile silicone is preferably from 1:100 to 50:1, more preferably from 1:20 to 5:1, even more preferably from 1:10 to 3:1, still even more preferably from 1:4 to 1:1.

Functionalized silicone as used herein means that the silicone is substituted by group containing heteroatom either forming part of the main polymer chain or more being carried by a side or pendant group carried by the polymeric backbone. Preferably, the heteroatom is selected from nitrogen and oxygen. For sake of clarity, the functionalized silicone as used herein includes dimethiconol. Preferably, the functionalized non-volatile silicone comprises amino-functionalised silicone and/or oxy-functionalised silicone. More preferably, the functionalized non-volatile silicone is selected from dimethiconol, aminosilicone, polyether-modified silicone, or a mixture thereof. Even more preferably, the non-volatile silicone comprises aminosilicone, polyether-modified silicone, or a mixture thereof. Still even more preferably the non-volatile silicone comprises aminosilicone, polyethylene glycol modified silicone or a mixture thereof. Most preferably the non-volatile silicone comprises polyethylene glycol modified silicone.

The composition may comprise non-volatile silicone which is not functionalized silicone. Preferably, the amount of function non-volatile silicone is at least 30% by weight of the total non-volatile silicone, more preferably 40 to 100% and even more preferably 50 to 100% by weight of the total non-volatile silicone. Still even more preferably, the functionalized non-volatile silicone accounts for 75 to 100% by weight of the total non-volatile silicone in the composition. Most preferably, the functionalized non-volatile silicone accounts for 100% by weight of the total non-volatile silicone in the composition.

The suitable dimethiconol preferably has a viscosity of from 10,000 to $10^9$ cSt (centi-Stokes) at 25° C., more preferably from 60,000 cSt to 500,000,000 cSt, even more preferably from 100,000 to 50,000,000 cSt, still even more preferably from 200,000 to 5,000,000 cSt, and most preferably from 500,000 to 2,000,000 cSt at 25° C.

Example of suitable dimethiconol for use in the compositions of the invention has a Sauter mean droplet diameter in the composition of less than 20 microns, preferably from 5 nm to 5 microns, more preferably from 20 nm to 2 microns, even more preferably from 40 nm to 1 micron, most preferably from 100 to 500 nm.

In general, polyether-modified silicone comprises a polydimethylsiloxane backbone with one or more polyoxyalkylene chains. The polyoxyalkylene moieties may be incorporated in the polymer as pendent chains or as terminal blocks. Such silicones are described in US Patent Application 2005/0098759 A1, and U.S. Pat. Nos. 4,818,421 and 3,299,112. More preferably, the polyether-modified silicone is polyethylene glycol modified silicone, polypropylene glycol modified silicone, polyethylene glycol and polypropylene glycol modified silicone, or a mixture thereof. Even more preferably the polyether-modified silicone is polyethylene glycol modified dimethicone. Exemplary commercially available polyether-modified silicones include DC 190, DC 193, all available from Dow Corning.

The suitable polyether-modified silicone preferably has a viscosity from 30 to 10,000 cSt (centi-Stokes) at 25° C., more preferably from 50 cSt to 1000 cSt, more preferably from 100 to 500 cSt, and even more preferably from 150 to 350 cSt at 25° C.

Aminosilicone means a silicone containing at least one primary, secondary or tertiary amine group, or a quaternary ammonium group. The primary, secondary, tertiary and/or quaternary amine groups may either form part of the main polymer chain or more preferably be carried by a side or pendant group carried by the polymeric backbone. Suitable aminosilicone for use with the invention are described for example in U.S. Pat. No. 4,185,087.

Aminosilicones suitable for use in the invention will typically have a mole % amine functionality in the range of from 0.1 to 8.0 mole %, preferably from 0.1 to 5.0 mole %, most preferably from 0.1 to 2.0 mole %. In general, the amine concentration should not exceed 8.0 mole %.

In a preferred embodiment, the aminosilicone is amodimethicone. Preferably, the amodimethicone has the general formula:

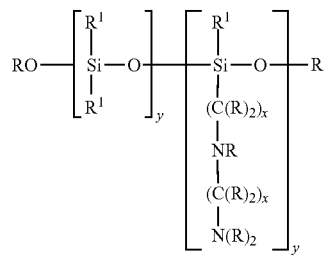

where each R is independently H, or a $C_{1-4}$ alkyl, preferably H; each $R^1$ is independently OR or a $C_{1-4}$ alkyl; and each x is independently an integer from 1 to 4 and each y is greater than zero and independently an integer to yield a polymer having a weigh average molecular weight from 500 to 1 million, and preferably from 750 to 100,000.

The emulsified aminosilicone suitable for use in the compositions of the invention preferably has a Sauter mean droplet diameter in the composition of from 10 nm to 20 microns, preferably from 30 nm to 5 microns, more preferably no greater than 1 micron, even more preferably from 20 nm 600 nm, and most preferably from 20 to 100 nm.

The viscosity of the aminosilicone itself is typically from 10 to 500,000 cSt (centi-Stokes) at 25° C., preferably from 100 cSt to 200,000 cSt, more preferably from 500 to 20,000 cSt, and even more preferably from 1,000 to 6,000 cSt.

Preferably, the non-volatile silicone comprises at least 30% of aminosilicone by weight of the non-volatile silicone, more preferably 40 to 100% and even more preferably 50 to 100% by weight of the total non-volatile silicone if the aminosilicone is present in the composition.

Depending on the end-use compositions according to the present invention will typically contain one or more of cationic surfactants, fatty alcohols, anti-dandruff agents, and cationic deposition polymers.

It is preferred that the composition comprises a cationic surfactant. Preferably the cationic surfactant is a quaternary ammonium salt. More preferably, the cationic surfactants have the formula $N^+R^1R^2R^3R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. Alkyl groups may be straight chain or branched and, for alkyl groups having 3 or more carbon atoms, cyclic. The alkyl groups may be saturated or may contain one or more carbon-carbon double bonds (e.g., oleyl). Preferably, the alkyl groups comprise one or more ester (—OCO— or —COO—) and/or ether (—O—) linkages within the alkyl chain. More preferably, the alkyl groups comprise one or more ether linkages within the alkyl chain. Even more preferably, the cationic surfactant is cetyltrimethylammonium chloride, behenyltrimethylammonium chloride or a mixture thereof. The most preferred cationic surfactant is behenyltrimethylammonium chloride.

Another example of a class of suitable conditioning surfactants for use in the invention, either alone or together with one or more other cationic surfactants, is a combination of (i) and (ii) below:

(i) an amidoamine corresponding to the general formula (I):

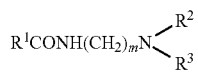

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups. Preferably, m is 2 or 3, i.e. an ethylene or propylene group.

Particularly preferred amidoamines useful herein are stearamidopropyldimethylamine, stearamidoethyldiethylamine, and mixtures thereof.

A protonating acid may be present. Acid may be any organic or mineral acid which is capable of protonating the amidoamine in the composition. Preferably, the acid is selected from the group consisting of acetic acid, tartaric acid, hydrochloric acid, fumaric acid, lactic acid and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant. Suitably, the acid is included in a sufficient amount to protonate more than 95 mole % (293 K) of the amidoamine present.

In compositions of the invention, the level of cationic surfactant will generally range from 0.01% to 10%, more preferably 0.05% to 7.5%, most preferably 0.1% to 5% by weight of the composition.

The composition preferably also incorporates a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.01 to 10%, preferably from 0.1% to 8%, more preferably from 0.2% to 7%, most preferably from 0.3% to 6% by weight of the composition.

The weight ratio of cationic surfactant to fatty alcohol is suitably from 1:1 to 1:10, more preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

It is preferred that the composition comprises a cationic deposition polymer, which may assist in deposition of ingredients in the composition. Preferably, the cationic deposition polymer is (or comprises) cationic polygalactomannan, especially guar or cassia derived polygalactomannan modified with hydroxypropyl trimonium chloride.

It is highly preferred that compositions according to the invention should contain from 0.01% to 2% wt. of the composition cationic deposition polymer, more preferably from 0.05 to 0.5% wt. and most preferably from 0.08 to 0.25% by weight of the composition.

The composition may additionally comprising antidandruff agent. Suitable antidandruff agents include compounds selected from azole based antifungal agents, octopirox, selenium sulfide, metal pyrithione salts, and mixtures thereof. The preferred azole based antifungal agents are ketoconazole and climbazole. Preferred metal pyrithione salts are zinc, copper, silver and zirconium pyrithione. The most preferred is zinc pyrithione.

Preferably, the antidandruff agent is present at from 0.01 to 5% wt. of the composition, more preferably from 0.1 to 2.5% wt. of the composition.

The composition of the invention may contain other ingredients for enhancing performance and/or consumer acceptability. Such ingredients include dyes and pigments, pH adjusting agents, pearlescers or opacifiers, viscosity modifiers, and preservatives or antimicrobials. Each of these ingredients will be present in an amount effective to accomplish its purpose. Generally these optional ingredients are included individually at a level of up to 5% by weight of the total composition.

The composition preferably comprises at least 30% of water by weight of the composition, more preferably from 35 to 99%, even more preferably from 45 to 95%, still even more preferably from 55 to 92%, most preferably from 65 to 90% by weight of the total composition.

Preferably the personal care composition is a hair treatment composition and more preferably a hair conditioner.

The invention will now be described with reference to the following non-limiting examples.

EXAMPLES

Materials

| Material | Supplier | Description |
| --- | --- | --- |
| Melamine Formaldehyde (MF) fluorescent capsules latex | Givaudan (Mechacaps perfecta P7) | particle diameter of 20 μm, particle solids content is 45.3%, 40% perfume loading in the slurry |
| Chitosan | Aldrich | cat. # 448877, deacetylation degree: 75-85% |
| Ethanol | Sinopharm Chemical | AR grade |
| Acetic Acid | Sinopharm Chemical | AR grade |
| Formic acid | Sinopharm Chemical | AR grade |
| Sodium chloride | Sinopharm Chemical | AR grade |

Example 1

This example demonstrates the preparation of particle.

1a) Preparation of Chitosan Complex 2.5 g of chitosan was added to 500 ml of 0.25% aqueous acetic acid solution and the mixture was agitated until chitosan dissolved completely, this yields a 0.5% Chitosan-Ac solution. Then 675 mg of arginine was added into the chitosan solution and the mixture was stirred overnight. The resultant aqueous product was denoted as Chitosan-Arg complex.

1b) Mixing of MF Slurry with Chitosan Complex 245 g of Chitosan-Arg complex solution was put into a beaker and homogenized. 70 g of diluted MF particles slurry (5 wt % of MF particle) was added dropwise to the Chitosan-Arg complex solution under homogenization. Then, the mixture was transferred to a flask and stirred at 75° C. The dosing ratio of chitosan complex to MF capsule was 1:3 (weight).

1c) Grafting of Chitosan Complex into MF Capsules 4.85 g of formaldehyde (37% aqueous solution) was diluted by 11 g of DI water in a flask. 2.5 g of melamine and 0.1 g of sodium chloride were then added. The pH of the mixture was adjusted to 8.9 by sodium carbonate solution. The mixture was stirred at room temperature for 10 minutes and then heated to 62° C. until it turned into a clear solution (melamine-formaldehyde prepolymer solution with prepolymer solids of 23.2 wt %).

After the temperature of the mixture prepared in section 1b) was raised to 75° C., 0.8 g of melamine-formaldehyde prepolymer solution was added and the pH of the final mixture was adjusted to 3.9 using aqueous formic acid solution. The mixture was stirred at 75° C. under 400 rpm for about two hours and then cooled to room temperature.

The resultant slurry was washed to remove the un-grafted Chitosan-Arg complex. The final concentrated slurry was denoted as MF-graft-Chitosan-Arg with particle solids content of around 13 wt %.

1d) Characterization of Chitosan Complex Modified MF Capsule

The zeta potentials of MF-graft-Chitosan-Arg and MF particle were measured by zeta potential analyzer (Zetasizer Nano ZS90, Malvern, USA) at 25° C. The particles were dispersed in water with solid content of 50 ppm and the pH of the dispersion was adjusted to about 7 for measurement. Each test was repeated three times. The zeta potential was 71 mV and −60 mV for MF-graft-Chitosan-Arg and MF particles respectively.

Example 2

This example demonstrates the preparation of hair conditioner.

TABLE 1

| | Samples (active wt %) | | | | |
| --- | --- | --- | --- | --- | --- |
| Ingredient | A | 1 | 2 | 3 | 4 |
| Cetearyl alcohol | 4.000 | 4.000 | 4.000 | 4.000 | 4.000 |
| Stearamidopropyl dimethylamine | 1.000 | 1.000 | 1.000 | 1.000 | 1.000 |
| Behenyltrimethyl-ammonium chloride | 0.700 | 0.700 | 0.700 | 0.700 | 0.700 |
| Lactic acid | 0.286 | 0.286 | 0.286 | 0.286 | 0.286 |
| Potassium chloride | 0.100 | 0.100 | 0.100 | 0.100 | 0.100 |
| Disodium EDTA | 0.100 | 0.100 | 0.100 | 0.100 | 0.100 |
| DC7134[a] | 1.225 | — | — | — | — |
| DC949[b] | — | 1.225 | — | — | — |
| DC8177[c] | — | — | 1.225 | — | — |
| DC1788[d] | — | — | — | 1.225 | — |
| DC193[e] | — | — | — | — | 1.225 |
| DMDM Hydantoin | 0.055 | 0.055 | 0.055 | 0.055 | 0.055 |
| CIT/MIT | 0.001 | 0.001 | 0.001 | 0.001 | 0.001 |
| Particle of Example 1 | 0.500 | 0.500 | 0.500 | 0.500 | 0.500 |
| Water | to 100 | to 100 | to 100 | to 100 | to 100 |

[a]DC7134, 70 wt % of active (6.8 wt % of amodimethicone and 63.2 wt % of dimethicone), INCI name: Dimethicone (and) Amodimethicone (and) PEG-7 Propylheptyl Ether (and) Cetrimonium Chloride ex Dow Corning.
[b]DC949, 35 wt % of active, INCI name: Amodimethicone and cetrimonium chloride and tridecenth-12, ex Dow Corning.
[c]DC8177, 13% of active, INCI name: amodimethicone (and) C12-14 Sec-Pareth-7 (and) C12-14 Sec-Pareth-5, ex Dow Corning.
[d]DC1788, 50% of active, INCI name: Dimethiconol (and) TEA-Dodecylbenzenesulfonate, ex Dow Corning.
[e]DC193, 100% of active, INCI name: PEG-12 Dimethicone, ex Dow Corning.

Example 3

This example demonstrates the effect of different silicones on deposition performance of MF-graft-Chitosan-Arg on virgin hair.

Three hair switches (virgin hair having length of 5.5 cm and weight of 750 mg, or tip hair having length of 5.5 cm and weight of 350 mg) were soaked into aqueous solution of 14 wt % of SLES at 40° C. with continuous shaking for 30 minutes. Then these hair switches were rinsed by tap water thoroughly and dried at ambient environment overnight.

The first hair switch was wetted with tap water and swung to remove excess water. The hair switch was rubbed with 0.12 g of sample in Table 1 and rinsed by 500 ml of tap water. The switch was swung dry and then immersed in a vial containing 20 milliliters of ethyl acetate for 30 minutes. 200 microliters of the extraction liquid was withdrawn from the vial and added to a 96-well microplate for fluorescence measurement (excitation 441 nm, emission 500 nm) to afford a reading of $E_1$.

The second switch was wetted with tap water and swung dry, to which 294 µl of the 0.5% of MF-graft-Chitosan-Arg particle was added. The switch was also extracted with 20 milliliters of ethyl acetate for 30 minutes. 200 microliters of the extraction liquid was withdrawn and added to the microplate and subjected to measurement using the aformentioned method and afforded a reading of $E_0$.

The third switch was extracted without particle adding step in 20 millilitres of ethyl acetate for 30 minutes. 200 microliters of the extraction liquid was taken to the microplate and afforded a reading $E_b$ upon fluorescence measurement.

The percent deposition (% deposition) was calculated according to the following equation:

$$\% \text{ Deposition} = \frac{E_1 - E_b}{E_0 - E_b} \times 100.$$

Table 2 shows the deposition results on virgin hair via incorporating the particles into conditioner base. The averages and standard derivations are calculated from 5 tests.

TABLE 2

| | | Deposition performance | |
|---|---|---|---|
| Sample | Silicone | Viscosity of silicone (cSt) | Deposition on virgin hair (%) |
| A | DC7134 | 600,000 | 5.3 ± 0.5 |
| 1 | DC949 | 2,000 | 8.2 ± 1.7 |
| 2 | DC8177 | 15,000 | 10.5 ± 2.1 |
| 3 | DC1788 | 1,000,000 | 7.7 ± 1.6 |
| 4 | DC193 | 260 | 11.5 ± 2.1 |

As can be seen from Table 2, it was surprisingly found that the deposition of the particle was greatly enhanced by incorporating silicones of the present invention into the hair conditioner.

The invention claimed is:
1. A personal care composition comprising:
   a) a particle comprising a chitosan salt at an outer surface of the particle; and
   b) 0.3 to 4% by weight of the composition is a functionalized non-volatile silicone,
      wherein the functionalized non-volatile silicone comprises polyethylene glycol modified silicone and optionally at least one of dimethiconol, aminosilicone, or any combination thereof;
      wherein the polyethylene glycol modified silicone is a polydimethylsiloxane backbone with one or more polyethylene glycol chains incorporated in the polymer as pendent chains or as terminal blocks;
      wherein the amount of the functionalized non-volatile silicone is greater than 20% by weight of the total % by weight of non-volatile silicone present in the personal care composition; and
      wherein the weight ratio of the particle to the functionalized non-volatile silicone is from 1:4 to 1:1.
2. The composition according to claim 1 wherein the chitosan salt is chitosan-amino acid salt.
3. The composition according to claim 1 wherein the particle comprises benefit agent inside of an inner shell, and an outer shell comprising the chitosan salt at the outer surface of the particle.
4. The composition according to claim 3 wherein the benefit agent is a fragrance.
5. The composition according to claim 3 wherein the inner shell comprises water insoluble non-polysaccharide polymer, water insoluble inorganic salt or a mixture thereof.
6. The composition according to claim 5 wherein the inner shell comprises polystyrene, polyvinyl alcohol, polyacrylate, polymethacrylates, polyolefins, aminoplast polymer, polyacrylamide, acrylate-acrylamide copolymer, melamine-formaldehyde condensate, urea-formaldehyde condensate, polyurethane, polysaccaharide or a mixture thereof.
7. The composition according to claim 1 wherein the particle has an average particle diameter of 0.5 to 20 µm.
8. The composition according to claim 3 wherein the chitosan salt is bonded to the inner shell by means of covalent bond.
9. The composition according to claim 1 wherein the functionalized non-volatile silicone has viscosity of 50 to 200,000 cSt.
10. The composition according to claim 1 wherein the composition additionally comprises a cationic surfactant.
11. The composition according to claim 1 wherein the composition is a hair conditioner.

* * * * *